United States Patent [19]

Blatchford

[11] 4,351,070
[45] Sep. 28, 1982

[54] ARTIFICIAL LEG WITH STABILIZED KNEE MECHANISM

[75] Inventor: Brian G. Blatchford, Basingstoke, England

[73] Assignee: Chas. A. Blatchford & Sons Limited, Hampshire, England

[21] Appl. No.: 183,997

[22] Filed: Sep. 4, 1980

[30] Foreign Application Priority Data

Sep. 7, 1979 [GB] United Kingdom ............... 7931086

[51] Int. Cl.³ .......................... A61F 1/04; A61F 1/08
[52] U.S. Cl. .......................................................... 3/27
[58] Field of Search ...................................... 3/22–28, 3/2

[56] References Cited

U.S. PATENT DOCUMENTS 3,666,299  5/1972  Bulter ................................. 3/27 X

FOREIGN PATENT DOCUMENTS 26622   12/1906  Austria .................................... 3/27
457809  6/1950   Italy ........................................ 3/27
132533  2/1921   United Kingdom ..................... 3/27
184571  8/1922   United Kingdom .
779087  7/1957   United Kingdom .
1213855 11/1970  United Kingdom .
1303738 1/1973   United Kingdom .
1534181 11/1978  United Kingdom .

OTHER PUBLICATIONS

Orthopaedic Appliances Atlas, vol. 2 (Artificial Limbs), J. W. Edwards, Ann Arbor, Michigan, 1960, pp. 197–198.

Primary Examiner—Ronald L. Frinks
Attorney, Agent, or Firm—Cushman, Darby & Cushman

[57] ABSTRACT

An artificial leg for an above-knee amputation. The leg includes a device for restraining knee flexion and means in which motion is produced in response to the application of torque about the hip axis. Mechanical means is provided to transfer and apply such motion to the restraining device so as either to cause the restraining device to restrain knee flexion or to release, or assist in releasing, restraint of knee flexion.

6 Claims, 2 Drawing Figures

ARTIFICIAL LEG WITH STABILIZED KNEE MECHANISM

FIELD OF THE INVENTION

This invention relates to an artificial leg having a stabilized knee mechanism.

DESCRIPTION OF THE PRIOR ART

The use of a "stabilized" knee mechanism in artificial leg is well known, examples having been disclosed in British Pat. Nos. 779,087 and 1,534,181. In these known examples, the function of a stabilized knee mechanism is to restrain, that is, to resist or prevent, flexion of the knee joint when the leg is bearing the wearer's weight during the stance phase and to allow flexion during the swing phase when the weight has been transferred to the other leg. Thus it is known to resist knee joint movement by sensing the application of a compressive load on the knee joint, as occurs when the wearer puts his weight on the leg, and causing a friction band or brake to act upon a rotating drum in the knee. The load takes the form of a force acting at the knee axis and having its major component in a direction approximately parallel to the shin portion of the leg.

A problem associated with known stabilized knee mechanisms is timing the release of the knee restraint to occur at the correct moment, i.e. during the period when the wearer's weight is being transferred to the other leg prior to the leg in question being lifted from the ground for the swing phase. To obtain a relatively natural gait it is important that release should occur before all of the wearer's weight has been removed from the leg. This requirement has been met with varying degrees of success by known weight-sensing stabilized knee mechanisms, but the problem remains in that careful adjustment is required to obtain on the one hand virtually instantaneous restraint when weight is placed on the leg at the beginning of the stance phase, and on the other hand correct release of the restraint towards the end of the stance phase with part of the wearer's weight remaining on the leg.

It is also known, from one proposed construction to overcome the problem referred to above, to control knee stabilization by sensing the hip torque exerted in the residual hip joint of the wearer's stump, but this known proposed construction includes a hip torque sensor, a knee angle sensor, a microcomputer to receive input signals from the sensors, a servomotor controlled by the computer, and a hydraulic device controlled by the servomotor, the hydraulic device controlling flexion of the leg about the knee axis. This construction is rather complex and sophisticated and hence necessarily somewhat expensive and bulky.

SUMMARY OF THE INVENTION

It is an object of this invention to provide a solution to the problem referred to above, using relatively simple and inexpensive means.

According to this invention, an artificial leg for a wearer with an above-knee amputation includes a device for restraining knee flexion, a mechanism in which motion is produced in response to the application of torque about the hip axis, and a mechanical means for transferring and applying the said motion to the restraining device so as either (i) to cause the restraining device to restrain knee flexion or (ii) to release, or to assist in releasing, restraint of knee flexion. By causing the restraining device to restrain, that is to resist or prevent, knee flexion in response to a hip torque tending to move the thigh rearwards, i.e. a hip extension torque, the knee can be made to resist or prevent flexion at the beginning of and during the stance phase and to become free before the end of the stance phase and before the whole of the wearer's weight has been transferred to the other leg. In this way the natural actions of the stump to stabilize the leg on contact of the heel with the ground are used to stabilize the artificial knee, and similarly, the natural actions of the stump used to flex the knee in the walking cycle are used to remove, or to assist in removing, the restraint from the knee. These characteristics can be used to achieve a more natural gait.

Preferably the means in which motion is produced in response to the application of hip torque comprises a linkage connecting a movable lower portion of the thigh component of the leg to the main portion of the thigh component, the instantaneous center of rotation of the lower portion relative to the main portion being at or near the wearer's natural hip joint axis. Motion in the linkage may be applied to the knee flexion restraining device by a lever-type mechanism, the restraining device being in the form of for example a friction band brake operating on a rotatable drum mounted on the shin portion of the leg.

If the instantaneous center of rotation of the linkage coincides with the natural hip joint axis, the linkage is insensitive to direct linear (i.e. weight-dependent) forces on the hip joint and is only responsive to torque about the hip joint.

In the above-mentioned preferred form there is a direct mechanical connection between the linkage and a friction band brake operating on the external surface of the rotatable drum. This direct connection provides a virtually instantaneous response to changes in hip torque and also a measure of feedback to the wearer, both of which features are important in enabling the wearer to 'feel' control of the knee and to develop a good gait. It is desirable that there should be a minimum storage of energy in the components used to apply the restraining force and that the components of the linkage in particular should be rigid and should only be required to move by small amounts to achieve the knee flexion restraining action.

An important advantage of a leg in accordance with the invention is that the knee may be produced with relatively few and simple parts. It is therefore relatively simple and inexpensive to manufacture, and furthermore offers good reliability and ready serviceability.

BRIEF DESCRIPTION OF THE DRAWINGS

An embodiment of the invention will now be described by way of example, with reference to the drawing in which.

DESCRIPTION OF THE PREFERRED EMBODIMENT

Figure 1:
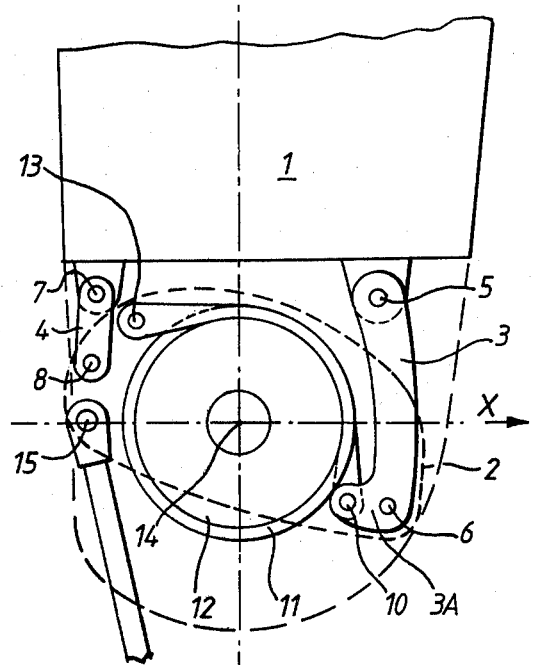
FIG. 1 is a diagrammatic side view of a hip torque sensing linkage connected to a friction brake.

Referring to FIG. 1, in which the front of the leg is indicated by the arrow X, the thigh component of an artificial leg has a main portion 1 and movable lower portion 2 pivotally connected to the main portion by two links 3 and 4, pin-pointed at 5, 6 and 7, 8 respectively. The links 3 and 4 are paired, i.e. they have corresponding links on the other side of the movable portion 2 which are not seen in FIG. 1. These two links together with the two thigh portions 1 and 2 form a "4-bar" linkage whose geometrical characteristics are such that the lower thigh portion 2 is rotatable relative to the main portion 1 about an instantaneous center of rotation 9 (FIG. 2) which in this embodiment is arranged to be substantially coincident with the wearer's natural hip joint axis when the links are in the position shown.

The front link 3 has a rearward, cranked extension 3A with a third pivot connection 10 to one end of a flexible brake band 11 which is wrapped around a rotatable drum 12 fixed to the shin component (not shown) of the leg. The other end of the band 11 is attached at 13 to the lower thigh portion 2, and the drum 12 is rotatable about a knee axis 14. The drum and the brake band together constitute a knee flexion restraining device in the form of a friction brake which resists or prevents motion of the shin component with respect to the thigh component when the brake band is tensioned by a downward force $P_1$ (FIG. 2) applied by lever action of the link 3, 3A about the pin-joint 6. Thus the link 3,3A constitutes a lever having a fulcrum at the pin-point 6.

Figure 2:
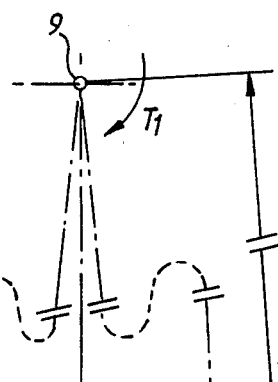
FIG. 2 is a diagram showing the force relationships between the moving parts of the linkage of FIG. 1.
Figure 2:
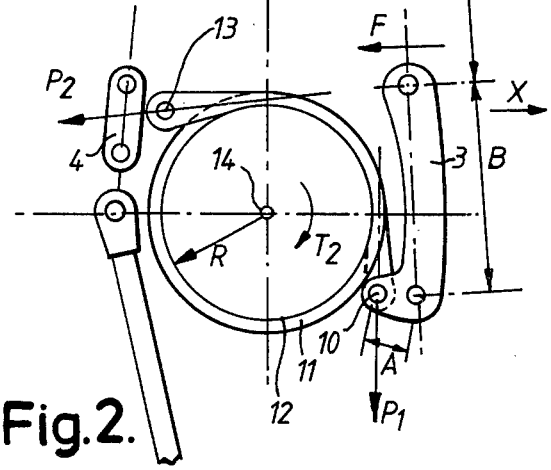

Stabilizing action of the knee occurs as follows. Referring to FIG. 2, when a hip extension torque $T_1$ is exerted by the wearer, a force F is applied to the upper end of the front link 3, resulting in the application at joint 10 of a force $P_1 = F \cdot A^B$ to the end of the brake band 11. If now an attempt is made to flex he knee joint (i.e. to rotate the drum 12 clockwise), friction between the band and drum causes the tension in the band to increase along the band until at the opposite end joint 13 the limiting force at the point of slipping is $P_2 = P_1 e^{\mu \theta}$, where $\mu$ is the coefficient of friction between the band 11 and the drum 12, and $\theta$ is the angle of wrap of the band 11 about the drum 12. The above expression may be used in conjunction with measured values of typical hip and knee torques to calculate a suitable value for $\theta$ which in this embodiment is equivalent for example to approximately 1¼ turns between the joints 10 and 13. FIG. 1 also shows the upper end of a known swing phase control device attached to the lower thigh portion 2 at 15.

The mechanism shown in the drawing requires means for maintaining it in, or returning it to, a neutral, non-restraining position when the hip extension torque is not present. Such means is not shown but may comprise in known manner a spring or a length of elasticated cord. Alternatively, one or both of the links 3 and 4 could be made from a flexible material, with one or both pin-joints of each link being replaced by a non-pin-jointed connection, using the flexibility of the material to provide a restoring or self-centering force.

The instantaneous center of rotation 9 coincides with the natural hip axis only in one position of the links 3 and 4. Therefore, if it is desired to produce a mechanism which is virtually insensitive to a linear, weight-dependent load on the leg, it is advantageous to minimize movement of the links. However, the invention is not limited to stabilizing mechanism which is insensitive to weight-dependent load, and linkage may be designed to have an instantaneous center of rotation 9 which deviates from coincidence with the natural hip joint axis, so as deliberately to introduce a degree of weight sensitivity to assist the stabilizing action of the knee if required, or to reduce or release the stabilizing action. For example, using the inherent movement of the instantaneous center of rotation of a 4-bar linkage, the center 9 may be allowed to move rearwardly as the linkage is deflected from its relaxed position, so as to add weight-derived stabilization as a result of the hip extension torque. Provision may be made for the position of one or more of the linkage pivots (5,6,7,8) to be adjustable, enabling the position of the instantaneous center 9 to be altered, or the ratio $B^4$ to be altered to suit different wearers. Also, for example, on hip flexion, the torque is removed, which would remove the weight-derived knee stabilization. Thus hip flexion, in an artificial leg in accordance with the invention, could be used to control, or assist in controlling, a restraining device which resists or prevents knee flexion. It is also possible to provide an inherent amount (which can be quite small) of weight sensitivity to assist the stabilizing action of the restraining device, by for example tilting the linkage backwards. Thus as seen in FIG. 1 the joint 7 could be placed slightly lower than the joint 5 with reference to the horizontal plane through the knee axis 14. This would cause the instantaneous center 9 always to be slightly behind the natural hip joint axis, which would make the knee mechanism normally weight-sensitive. In such a construction hip extension torque could be used to increase the stabilizing effect (i.e. the knee flexion restraint) and hip flexion torque could be used to reduce or even to remove the knee flexion restraint, or it could be used to assist some other device to reduce or remove the knee flexion restraint. Further, such reduction or removal of restraint could be made, by appropriate adjustment of the positions of the joints, or lengths of the linkages, to take place at that moment in time when the knee is to be bent in walking, for instance just before the termination of the stance phase. In this connection it may be mentioned that a feature of the known weight-sensitive knee mechanisms is the need to bend the knee joint before such termination, while the foot is still in contact with the ground and consequently while the leg is still weight-bearing. This means that although it is desirable to release the knee flexion restraint before the foot leaves the ground, nevertheless the inherent action of the weight-sensitive knee mechanism is to prevent such release, and this is a disadvantage. It would be possible to avoid this disadvantage with an artificial leg in accordance with the present invention.

Alternative embodiments (not shown) within the scope of the invention include a knee mechanism having an internal brake shoe operating on the internal surface of the rotatable drum. In addition, one or both links of the 4-bar linkage may comprise blocks of flexible material. The friction brake may be replaced by a pneumatic or hydraulic piston and cylinder arrangement similar to a known swing phase control device, the arrangement including a valve actuated mechanically by he hip torque sensing linkage to vary the resistance to knee flexion.

I claim:

1. An artificial leg for a wearer with an above-knee amputation comprising: a device for restraining knee flexion; means in which motion is produced in response to the application of torque about the natural hip axis of the wearer; and mechanical means which is adapted to apply said motion to the restraining device so as either (i) to cause the restraining device to restrain knee flexion or (ii) to release or to assist in releasing restraint of knee flexion, said means in which motion is produced being an upper leg component which includes an upper part, a lower part movably connected to the upper part and connecting means connecting said upper and lower parts and permitting movement of said lower part in the anterior/posterior direction such that said lower part moves about an instantaneous center of rotation coincident with or close to the said natural hip axis, said connecting means including a link pivotally connected at its upper end to said upper part and pivotally connected at its lower end to said lower part.

2. An artificial leg according to claim 1 wherein the device for restraining knee flexion comprises a drum fixed to a lower leg component and a brake member engaging the drum and connected to said mechanical means.

3. An artificial leg according to claim 1 wherein said mechanical means includes a lever connected to the restraining device.

4. An artificial leg according to claim 1 wherein said mechanical means includes a lever connected to the restraining device and forming part of said pivotally connected link at its lower end.

5. An artificial leg for a wearer with an above-knee amputation comprising: a device for restraining knee flexion; means in which motion is produced in response to the application of torque about the natural hip axis of the wearer; and mechanical means which is adapted to apply said motion to the restraining device so as either (i) to cause the restraining device to restrain knee flexion or (ii) to release or to assist in releasing restraint of knee flexion, said means in which motion is produced being an upper leg component which includes an upper part, a lower part movably connected to the upper part and connecting means connecting said upper and lower parts and permitting movement of said lower part in the anterior/posterior direction such that said lower part moves about an instantaneous center of rotation conincident with or close to the said natural hip axis, said connecting means including a four-bar linkage, the first bar being said upper part, the fourth bar being said lower part, and the second and third bars being anterior and posterior link members pivotally connected at their respective upper and lower ends to said upper and lower parts, the link members constituting connecting members between said upper and lower parts.

6. An artificial leg according to claim 5 wherein the relative dispositions of the pivotal connection of the said anterior and posterior link members is such that they produce said instantaneous center of rotation.

* * * * *

UNITED STATES PATENT AND TRADEMARK OFFICE
CERTIFICATE OF CORRECTION

PATENT NO. : 4,351,070
DATED : September 28, 1982
INVENTOR(S) : Brian Geoffrey Blatchford It is certified that error appears in the above—identified patent and that said Letters Patent is hereby corrected as shown below:

Column 2, last line "pin-pointed" should read --pin-jointed--.

Column 3, line 24, "pin-point" should read --pin-joint--.

Signed and Sealed this

Twenty-seventh Day of December 1983

[SEAL]

Attest:

GERALD J. MOSSINGHOFF

Attesting Officer     Commissioner of Patents and Trademarks